United States Patent [19]

Vita

[11] Patent Number: 4,562,178

[45] Date of Patent: Dec. 31, 1985

[54] USE OF DIETHYLAMINOETHYLDEXTRAN (DEAE-D) AS AN ANTIHYPERINSULINEMIC DRUG

[75] Inventor: Filippo Vita, Rome, Italy

[73] Assignee: Medosan Industrie Biochimiche Riunite S.p.A., Albano Laziale, Italy

[21] Appl. No.: 683,676

[22] Filed: Dec. 19, 1984

[30] Foreign Application Priority Data

Dec. 23, 1983 [IT] Italy ................ 49659 A/83

[51] Int. Cl.⁴ .............................. A61K 31/70
[52] U.S. Cl. ..................................... 514/59
[58] Field of Search ............ 424/180; 538/112; 514/59

[56] References Cited

U.S. PATENT DOCUMENTS 4,160,826  7/1979  Fischetti .................. 424/180

Primary Examiner—Alan Siegel
Attorney, Agent, or Firm—Cushman, Darby & Cushman

[57] ABSTRACT

Diethylaminoethyldextran (DEAE-D), administered as an antihyperinsulinemic agent, performs an inhibitory action on hyperinsulinemia through a mediation of gastroenterohormones.

4 Claims, No Drawings

USE OF DIETHYLAMINOETHYLDEXTRAN (DEAE-D) AS AN ANTIHYPERINSULINEMIC DRUG

BACKGROUND OF THE INVENTION

1. Field of the Invention

The present invention relates the use of diethylaminoethyldextran (DEAE-D) as an antihyperinsulinemic drug, while its use up to now has been as an antihyperlipemic agent in a general sense, since it acts on lipid components. It has been determined that this drug, as a function of dosage and administration schedule, has an inhibitory effect on hyperinsulinemia, documented by significant clinical results.

DEAE-D is a practically inocuous drug which is of significant interest as an antihyperinsulinemic drug.

2. Description of the Prior Art

Previous experience did not predict the significant action of the drug at the pancreatic and extrapancreatic level, because the detailed mechanisms of gastroenterohormone mediation were unknown. These are currently the subject of additional study, and have been identified as an extra-cerebral extraversion of endocrine action peptides (APUD system and the like).

Furthermore, the possibility had never been studied, demonstrated or presumed that the drug might intervene in a direct and/or indirect way on the phenomenon of raised insulin levels, the physiopathological importance of which has been shown clearly in recent studies.

Hyperinsulinemia states in fact play a very important role in the most modern nosographic view of various dysmetabolic-dysendocrine conditions.

SUMMARY OF THE INVENTION

Object of the invention is the utilisation of diethylaminoethyldextran (DEAE-D) for the treatment of hyperinsulinemic subjects in order to decrease the excess insulin level in the blood.

It has also been found that a pharmaceutically effective amount is approximately 500 mg DEAE-D per 20 Kg body weight.

The treatment is by oral administration and can be used particularly in endogenous and reactive hypoglycemia as well as in hyperinsulinemic and pre-clinical diabetes.

Our clinical studies using the drug in various cases of dysmetabolism suggested that there were some effects other than that of lipid function modulation, which was the only one known previously. Careful analysis of previous studies using DEAE-D showed the antisteatogenetic effect of the drug, due to its fats chelating action at the level of the intestinal lumen. Therefore, the site of the molecule's extra plasmatic action is well known precisely because its absorption is impossible. This led us to deepen the hormonal study of the subjects treated with DEAE-D. We thus observed significant modifications in the insulinemia, and embarked on a research program designed to enrich and deepen our understanding.

A brief introduction is necessary to the endocrine-metabolic movements which are behind the modifications in hormonal balance during meals.

Eating sets off at the jejunum-ileum level a series of physiopathological events which are the center of the so-called enterinsular axis. In fact, various substances of a polypeptide nature called "gastroenterohormones" have been described which are capable of responding to lipid, protein and glycidic stimuli with a massive immission of insular hormones (insulin, somatostatin and others).

In practice, the presence of alimentary principles at the jejunum-ileum level leads to an increase to the portal level of gastrin, enteroglucagon, VIP, GIP and others less well known. These gastroenterohormones, through a short feed-back mechanism, lead to a rapid increase of insulin.

The rise in insulinemia has, among others, the effect of inhibiting lipolysis as well as inducing hypoglycemia. Subsequently other controinsular hormones modulate the hypoglycemizing and hypo-NEFA-emic effects.

For example, in cases of obesity and hyperinsulinemic diabetes these delicate homeostasis mechanisms are affected, with the result of hyperinsulinemia which is basal as well as post-prandial. The most tangible effect of this protracted increase in the hormone circuit is the tendency for transitory hypoglycemia with immediate hypothalamic stimulus of the so-called "hunger center." In fact, classic hunger-suppressing drugs acts by crossing the hematoencephalic barrier and decreasing the hunger stimulation threshold at the hypothalamic level.

I. Clinical Tests

Materials and Methods

The experimental model was 12 selected hospitalized patients suffering from hyperinsulinemia associated with other pathologies in order to show:

(a) the response of insulinemia to DEAE-D
(b) the dosage of the drug required for those ends
(c) the useful administration times
(d) the hormonal response times
(e) any intolerance to the drug
(f) biological verification of the results with the corroboration of the presumed mechanism of action.

Eight of these patients were placed on a diet of 1000–1200 calories, balanced in glycides, peptides and lipids, associated with the administration of DEAE-D in a dose of 500 mg/Kg of body weight, in a single pill at the morning meal. The serum insulin level was determined from blood samples drawn every 30 minutes for 120 minutes, by centrifugation and R.I.A. measurement of the insulin expressed in $\mu$ units/ml.

Four of the patients were placed on a controlled fast therapy, with DEAE-D administration in the dosages and schedules as described above. Insulin levels were also tested in these patients every 30 minutes for 120 minutes.

Example 1

M.V., 23 years, female
Hyperinsulinemia associated with hyperprolactinemia with oligomenorrhea
Free balanced normal calorie diet,
+3 g of DEAE-D in a single pill at 13:00
Blood samples every 30 minutes after the meal, and insulinemia measured using the R.I.A. method.
The following values were obtained:

| | |
|---|---|
| basal 30 minutes after meal | 65.8 micro units/ml |
| 60 minutes | 27.5 |
| 90 minutes | 25.4 |
| 120 minutes | 17.4 |

No associated pharmacological therapy
Short and medium term side effects: none

|                        |                                                                                                                                                                                                                                                                                                                                                                                                                    |
| ---------------------- | ------------------------------------------------------------------------------------------------------------------------------------------------------------------------------------------------------------------------------------------------------------------------------------------------------------------------------------------------------------------------------------------------------------------ |
|                        | Tolerance: optimal                                                                                                                                                                                                                                                                                                                                                                                                 |
| Example 2              |                                                                                                                                                                                                                                                                                                                                                                                                                    |
| P.M., 19 years, female | Hyperinsulinemia, hyperprolactinemia and gonadotropin disturbances<br>Free normal calorie balanced diet<br>+2.5 g DEAE-D<br>Blood samples drawn every 30 minutes after the meal, and insulinemia measured using the R.I.A. method<br>The following values were obtained:<br>basal 30 minutes after meal   62.1 micro units/ml<br>  60 minutes   46.5<br>  90 minutes   25.8<br>  120 minutes   17.5<br>No associated pharmacological therapy<br>Short and medium term side effects: none<br>Tolerance: optimal |
| Example 3              |                                                                                                                                                                                                                                                                                                                                                                                                                    |
| A.C., 59 years, female | Hyperinsulinemia associated with hyperuricemia and hydroelectrolytic disturbances<br>Free normal calorie balanced diet<br>+2.5 g DEAE-D<br>Blood samples drawn every 30 minutes after the meal, and insulinemia measured using the R.I.A. method<br>The following values were obtained:<br>basal 30 minutes after meal   55.4 micro units/ml<br>  60 minutes   40.9<br>  90 minutes   38.4<br>  120 minutes   17.8<br>No associated pharmacological therapy<br>Short and medium term side effects: none<br>Tolerance: optimal |
| Example 4              |                                                                                                                                                                                                                                                                                                                                                                                                                    |
| N.M.S., 52 years, female | Hyperinsulinemia and climacteric syndrome<br>Free normal calorie balanced diet<br>+2 g DEAE-D<br>Blood samples drawn every 30 minutes after the meal, and insulinemia measured using the R.I.A. method<br>The following values were obtained:<br>basal 30 minutes after meal   34.3 micro units/ml<br>  60 minutes   22.3<br>  90 minutes   17.2<br>  120 minutes   11.2<br>No associated pharmacological therapy<br>Short and medium term side effects: none<br>Tolerance: optimal |
| Example 5              |                                                                                                                                                                                                                                                                                                                                                                                                                    |
| L.R., 55 years, female | Hyperinsulinemia in type 2° diabetes<br>Free normal calorie balanced diet<br>+3 g DEAE-D<br>Blood samples drawn every 30 minutes after the meal, and insulinemia measured using the R.I.A. method<br>The following values were obtained:<br>basal 30 minutes after meal   64.0 micro units/ml<br>  60 minutes   33.0<br>  90 minutes   29.2<br>  120 minutes   22.8<br>No associated pharmacological therapy<br>Short and medium term side effects: none<br>Tolerance: optimal |
| Example 6              |                                                                                                                                                                                                                                                                                                                                                                                                                    |
| G.P., 33 years, female | Hyperinsulinemia and hypothyroidism<br>Free normal calorie balanced diet<br>+2 g DEAE-D<br>Blood samples drawn every 30 minutes after the meal, and insulinemia measured using the R.I.A. method<br>The following values were obtained:<br>basal 30 minutes after meal   59.4 micro units/ml<br>  60 minutes   21.1<br>  90 minutes   18.5 |

|                        |                                                                                                                                                                                                                                                                                                                                                                                                                    |
| ---------------------- | ------------------------------------------------------------------------------------------------------------------------------------------------------------------------------------------------------------------------------------------------------------------------------------------------------------------------------------------- |
|                        | 120 minutes   14.0<br>No associated pharmacological therapy<br>Short and medium term side effects: none<br>Tolerance: optimal |
| Example 7              |                                                                                                                                                                                                                                                                                                                                           |
| A.A., 59 years, male   | Hyperinsulinemia in type 2 diabetes<br>Free normal calorie balanced diet<br>+2.5 g DEAE-D<br>Blood samples drawn every 30 minutes after the meal, and insulinemia measured using the R.I.A. method<br>The following values were obtained:<br>basal 30 minutes after meal   61.1 micro units/ml<br>  60 minutes   59.0<br>  90 minutes   22.3<br>  120 minutes   21.2<br>No associated pharmacological therapy<br>Short and medium term side effects<br>Tolerance: optimal |
| Example 8              |                                                                                                                                                                                                                                                                                                                                           |
| L.M., 19 years, female | Hyperinsulinemia with ovary disturbances<br>Free normal calorie balanced diet<br>+2 g DEAE-D<br>Blood samples drawn every 30 minutes after the meal, and insulinemia measured using the R.I.A. method<br>The following values were obtained:<br>basal 30 minutes after meal   59.2 micro units/ml<br>  60 minutes   34.3<br>  90 minutes   25.7<br>  120 minutes   14.6<br>No associated pharmacological therapy<br>Short and medium term side effects: none<br>Tolerance: optimal |
| Example 9              |                                                                                                                                                                                                                                                                                                                                           |
| P.DiF., 19 years, female | Constitutional hyperinsulinemia with ovary disturbances and oligomenorrhea<br>Complete fast for 48 hours, fed with phleboclysis to maintain hydroelectrolyte balance<br>Insulin levels were measured 30 minutes after administration of 2 g of DEAE-D<br>The following values were obtained:<br>at 30 minutes   15.7 micro units/ml<br>  60   14.0<br>  90   12.7<br>  120   10.5<br>No associated pharmacological therapy<br>Short and medium term side effects: none<br>Tolerance: optimal |
| Example 10             |                                                                                                                                                                                                                                                                                                                                           |
| E.C., 33 years, female | Hyperinsulinemia with severe type 2 diabetes and hypercortisolemia<br>Complete fast for 24 hours, fed with phleboclysis<br>Insulin levels were measured 30 minutes after administration of 2 g of DEAE-D<br>The following values were obtained:<br>at 30 minutes   24.8 micro units/ml<br>  60   21.0<br>  90   20.1<br>  120   20.2<br>No associated pharmacological therapy<br>Short and medium term side effects: none<br>Tolerance: optimal |
| Example 11             |                                                                                                                                                                                                                                                                                                                                           |
| S.A., 40 years, male   | Hyperinsulinemic diabetes<br>Complete fast for 24 hours, fed with<br>Insulin levels were measured 30 minutes after administration of 2 g of DEAE-D<br>The following values were obtained:<br>at 30 minutes   34.5 micro units/ml<br>  60   31.5<br>  90   27.8<br>  120   26.2<br>No associated pharmacological therapy |

-continued

|  | Short and medium term side effects: none |
|---|---|
|  | Tolerance: optimal |
| Example 12 | |
| S.E., | Hyperinsulinemic type 2 diabetes |
| 47 years, | Complete fast for 24 hours, fed with |
| male | phleboclysis |
|  | Insulin levels were measured 30 minutes after administration of 2 g of DEAE-D |
|  | The following values were obtained: |
|  | at 30 minutes    32.1 micro units/ml |
|  | 60    27.2 |
|  | 90    26.3 |
|  | 120    26.6 |
|  | No associated pharmacological therapy |
|  | Short and medium term side effects: none |
|  | Tolerance: optimal |

In Examples 1 to 8, a mean critical decrease in insulinemia of more than ⅔ of the maximum value was noted within 60–90 minutes, on the average; a reduction over time was also noted, even below the initial basal level. A "sense of satiety" was reported in all cases, and a sudden weight loss (from 400 to 600 grams) was observed the day after treatment with DEAE-D.

In Examples 9 to 12, in which the subjects were kept fasting and treated with DEAE-D, the results showed a small decrease in basal hyperinsulinemia, even 2 hours after administration of DEAE-D. The drug was well tolerated when fasting, as well.

The above results confirm the effect of the drug on the stimulus the alimentary precursors exert on the gastroenterohormones and the effect of the latter on insulinemia.

II. Clinical Tests

Materials and Methods 70 hospitalized subjects were studied, of both sexes, ranging in age from 18 to 65 years and divided into two groups.

The first group included 47 of these subjects selected on the basis of basic insulin values above normal (5–20 micro/Uml); the second group included 23 subjects with normal basal insulinemia.

The members of the first group had weights 18 to 62 Kg above ideal; the members of the second were normal in weight. Both groups were free of other endocrinopathies and organic pathologies. All subjects were given a standard normal calorie diet in the 10 days before the test.

On day A, they were given a 1500 Kcal meal, balanced in glucides, protein and lipids, at hour φ.

Serum insulinemia was measured on two samples using the R.I.A. method at time 0–30' (B), +30', +60', +90', +120 and some at +180 minutes.

Two days later (day B) the test was repeated with administration of a single pill at meal time (time φ), equivalent to a dose of 500 mg/Kg body weight.

The results of the first group are referred to in Table 1 and the results of the second group are referred to in Table 2 herinafter.

TABLE 1

| Case | B | +30' | +60' | +90' | +120' | +180' | |
|---|---|---|---|---|---|---|---|
| (1) | 28,6 | 102,6 | 98,4 | 80,6 | 76,4 |  | A |
|  | 26,4 | 80,8 | 62,4 | 48,9 | 30,1 |  | B |
| (2) | 26,2 | 116,8 | 121,0 | 80,3 | 78,2 |  | A |
|  | 30,1 | 90,6 | 70,4 | 48,2 | 26,1 |  | B |
| (3) | 40,1 | 136,2 | 112,2 | 108,6 | 90,0 |  | A |
|  | 36,6 | 102,0 | 84,2 | 68,3 | 40,1 |  | B |
| (4) | 21,8 | 128,0 | 132,7 | 102,6 | 90,4 |  | A |
|  | 28,2 | 90,2 | 74,6 | 46,2 | 26,1 |  | B |
| (5) | 36,7 | 144,2 | 131,6 | 126,6 | 112,0 |  | A |
|  | 34,2 | 100,2 | 86,1 | 48,6 | 31,2 |  | B |
| (6) | 32,6 | 134,6 | 132,4 | 128,2 | 99,6 |  | A |
|  | 28,9 | 126,3 | 94,2 | 94,6 | 32,2 |  | B |
| (7) | 44,6 | 180,6 | 168,4 | 136,0 | 121,8 |  | A |
|  | 40,2 | 132,2 | 90,6 | 62,2 | 34,8 |  | B |
| (8) | 28,6 | 118,6 | 124,4 | 90,2 | 88,4 |  | A |
|  | 30,1 | 100,4 | 79,9 | 44,2 | 21,6 |  | B |
| (9) | 31,0 | 116,6 | 102,2 | 108,4 | 78,2 |  | A |
|  | 29,2 | 80,6 | 59,2 | 37,8 | 26,8 |  | B |
| (10) | 21,6 | 90,6 | 86,2 | 70,4 | 69,2 |  | A |
|  | 24,1 | 71,2 | 46,6 | 29,7 | 16,2 |  | B |
| (11) | 32,4 | 134,2 | 126,6 | 118,3 | 90,6 |  | A |
|  | 30,6 | 92,4 | 84,2 | 56,4 | 31,6 |  | B |
| (12) | 38,1 | 164,2 | 138,6 | 141,0 | 112,8 |  | A |
|  | 36,2 | 102,6 | 80,3 | 61,6 | 44,2 |  | B |
| (13) | 36,1 | 160,0 | 142,2 | 90,6 | 108,2 | 90,4 | A |
|  | 40,4 | 144,2 | 102,8 | 80,5 | 61,8 | 34,6 | B |
| (14) | 27,6 | 118,6 | 90,2 | 90,6 | 86,1 |  | A |
|  | 33,8 | 102,4 | 86,6 | 60,2 | 40,8 |  | B |
| (15) | 28,2 | 116,2 | 96,4 | 92,6 | 80,4 |  | A |
|  | 24,6 | 80,6 | 59,8 | 40,2 | 26,1 |  | B |
| (16) | 30,6 | 164,2 | 113,6 | 128,8 | 102,2 |  | A |
|  | 28,8 | 108,6 | 80,2 | 62,1 | 36,4 |  | B |
| (17) | 38,2 | 129,0 | 141,8 | 109,8 | 99,2 |  | A |
|  | 30,1 | 96,2 | 74,4 | 36,8 | 28,2 |  | B |
| (18) | 26,1 | 132,2 | 112,4 | 98,4 | 76,2 |  | A |
|  | 30,8 | 102,0 | 72,7 | 48,3 | 26,4 |  | B |
| (19) | 29,1 | 136,0 | 127,2 | 96,2 | 88,8 |  | A |
|  | 34,6 | 96,2 | 70,1 | 41,8 | 28,0 |  | B |
| (20) | 26,6 | 98,2 | 84,6 | 79,2 | 80,3 |  | A |
|  | 24,1 | 78,2 | 46,3 | 22,0 | 24,6 |  | B |
| (21) | 24,6 | 124,1 | 108,7 | 96,2 | 94,6 |  | A |
|  | 30,1 | 99,7 | 64,6 | 45,0 | 31,2 |  | B |
| (22) | 29,0 | 116,2 | 99,8 | 96,4 | 87,2 |  | A |
|  | 24,6 | 78,6 | 43,6 | 32,4 | 21,8 |  | B |
| (23) | 27,4 | 131,6 | 108,0 | 11,2 | 96,3 |  | A |
|  | 24,2 | 86,2 | 64,8 | 50,2 | 30,0 |  | B |
| (24) | 28,4 | 102,0 | 90,6 | 108,2 | 80,4 | 82,6 | A |
|  | 18,2 | 96,2 | 80,4 | 62,1 | 58,6 | 30,8 | B |
| (25) | 22,8 | 88,6 | 90,1 | 78,8 | 66,2 |  | A |
|  | 26,2 | 70,6 | 56,2 | 47,1 | 28,8 |  | B |
| (26) | 28,6 | 86,3 | 80,6 | 78,6 | 68,8 |  | A |
|  | 24,0 | 72,6 | 58,8 | 42,2 | 23,8 |  | B |
| (27) | 26,2 | 96,3 | 88,8 | 89,2 | 78,6 |  | A |
|  | 24,8 | 80,4 | 70,2 | 58,6 | 18,4 |  | B |
| (28) | 31,0 | 126,6 | 108,2 | 102,8 | 84,6 |  | A |
|  | 27,8 | 116,4 | 86,2 | 61,6 | 40,4 |  | B |
| (29) | 28,6 | 121,0 | 108,8 | 104,6 | 92,4 |  | A |
|  | 24,8 | 90,4 | 60,6 | 46,2 | 19,6 |  | B |
| (30) | 21,8 | 98,1 | 86,3 | 84,2 | 76,6 |  | A |
|  | 26,8 | 64,1 | 51,8 | 42,6 | 24,2 |  | B |
| (31) | 32,8 | 142,6 | 126,2 | 131,8 | 98,6 |  | A |
|  | 34,6 | 100,8 | 80,3 | 64,6 | 40,2 |  | B |
| (32) | 31,8 | 102,6 | 86,4 | 94,2 | 78,6 |  | A |
|  | 36,0 | 89,9 | 80,4 | 48,2 | 30,6 |  | B |
| (33) | 28,6 | 90,0 | 102,2 | 86,6 | 80,4 |  | A |
|  | 30,1 | 68,6 | 46,6 | 42,1 | 26,6 |  | B |
| (34) | 46,2 | 146,0 | 128,3 | 102,6 | 100,8 |  | A |
|  | 34,4 | 126,3 | 92,1 | 78,0 | 40,4 |  | B |
| (35) | 28,6 | 121,6 | 116,2 | 109,3 | 86,2 |  | A |
|  | 31,2 | 88,6 | 70,1 | 52,6 | 28,9 |  | B |
| (36) | 36,2 | 108,2 | 100,8 | 102,6 | 90,1 |  | A |
|  | 32,2 | 100,2 | 90,6 | 64,2 | 30,0 |  | B |
| (37) | 40,2 | 142,0 | 134,2 | 126,6 | 100,2 | 88,6 | A |
|  | 36,7 | 124,6 | 100,2 | 70,4 | 46,1 | 24,8 | B |
| (38) | 26,6 | 131,0 | 124,6 | 100,2 | 86,4 |  | A |
|  | 28,2 | 104,4 | 88,0 | 60,4 | 32,2 |  | B |
| (39) | 36,7 | 64,2 | 98,4 | 46,4 | 55,2 | 48,8 | A |
|  | 32,4 | 62,0 | 46,2 | 54,3 | 31,2 | 18,6 | B |
| (40) | 25,0 | 109,2 | 116,6 | 92,2 | 76,3 |  | A |
|  | 23,2 | 102,0 | 64,2 | 42,6 | 28,3 |  | B |
| (41) | 31,4 | 94,2 | 86,6 | 83,8 | 91,4 | 64,2 | A |
|  | 26,5 | 92,0 | 64,3 | 46,5 | 32,2 | 18,2 | B |
| (42) | 24,8 | 84,5 | 92,8 | 78,1 | 74,2 |  | A |
|  | 30,2 | 60,3 | 58,2 | 40,6 | 18,6 |  | B |
| (43) | 37,0 | 142,0 | 102,8 | 98,2 | 68,8 |  | A |

TABLE 1-continued

| Case | B | +30' | +60' | +90' | +120' | +180' | |
|---|---|---|---|---|---|---|---|
| | 28,0 | 102,2 | 84,0 | 48,8 | 22,6 | | B |
| (44) | 28,6 | 116,2 | 94,6 | 102,8 | 80,2 | | A |
| | 24,8 | 104,6 | 74,2 | 56,6 | 38,8 | | B |
| (45) | 24,8 | 96,2 | 74,6 | 82,4 | 68,2 | | A |
| | 26,6 | 88,6 | 78,3 | 48,8 | 21,0 | | B |
| (46) | 38,0 | 142,3 | 124,2 | 94,6 | 78,8 | | A |
| | 34,6 | 108,0 | 84,2 | 49,9 | 28,2 | | B |
| (47) | 40,2 | 124,2 | 102,6 | 104,2 | 92,8 | 90,6 | A |
| | 34,6 | 102,0 | 76,2 | 68,8 | 50,6 | 32,3 | B |

A = insulinemia after a normal meal
B = insulinemia after a meal + DEAE-D

TABLE 2

| Case | B | +30' | +60' | +90' | +120' | |
|---|---|---|---|---|---|---|
| (1) | 12,3 | 86,4 | 78,6 | 66,4 | 64,2 | A |
| | 14,6 | 76,2 | 49,2 | 32,4 | 20,6 | B |
| (2) | 10,8 | 76,4 | 72,6 | 60,4 | 56,8 | A |
| | 12,6 | 62,2 | 41,8 | 30,2 | 26,1 | B |
| (3) | 9,6 | 114,2 | 100,6 | 92,4 | 84,1 | A |
| | 11,7 | 8,0 | 64,2 | 39,1 | 24,4 | B |
| (4) | 16,0 | 100,1 | 96,0 | 87,1 | 69,6 | A |
| | 14,2 | 82,6 | 64,2 | 47,2 | 28,4 | B |
| (5) | 12,4 | 74,2 | 64,2 | 54,6 | 48,8 | A |
| | 16,6 | 62,4 | 42,0 | 24,6 | 18,2 | B |
| (6) | 11,8 | 92,6 | 84,2 | 68,8 | 56,6 | A |
| | 14,2 | 72,6 | 49,9 | 36,6 | 19,8 | B |
| (7) | 12,3 | 82,0 | 77,6 | 61,5 | 64,6 | A |
| | 14,1 | 64,8 | 42,3 | 56,2 | 18,6 | B |
| (8) | 8,9 | 80,4 | 72,6 | 64,6 | 40,2 | A |
| | 14,1 | 60,2 | 39,6 | 30,1 | 18,2 | B |
| (9) | 11,6 | 70,4 | 62,6 | 58,8 | 50,4 | A |
| | 13,2 | 44,2 | 38,8 | 26,2 | 16,7 | B |
| (10) | 9,6 | 78,8 | 64,6 | 61,2 | 52,6 | A |
| | 12,6 | 67,8 | 42,3 | 40,8 | 26,2 | B |
| (11) | 11,8 | 64,6 | 66,2 | 58,6 | 49,9 | A |
| | 8,6 | 48,8 | 28,6 | 22,1 | 20,2 | B |
| (12) | 8,8 | 72,4 | 61,7 | 60,2 | 54,6 | A |
| | 14,1 | 58,9 | 37,4 | 28,6 | 18,8 | B |
| (13) | 9,2 | 90,6 | 78,8 | 70,2 | 54,6 | A |
| | 12,6 | 68,8 | 54,2 | 40,1 | 24,4 | B |
| (14) | 12,6 | 68,8 | 64,2 | 66,4 | 48,8 | A |
| | 11,2 | 54,0 | 40,1 | 32,7 | 22,0 | B |
| (15) | 8,2 | 78,2 | 64,4 | 57,0 | 59,2 | A |
| | 16,4 | 54,6 | 40,1 | 28,6 | 22,4 | B |
| (16) | 10,1 | 88,4 | 72,2 | 68,8 | 48,8 | A |

TABLE 2-continued

| Case | B | +30' | +60' | +90' | +120' | |
|---|---|---|---|---|---|---|
| | 14,3 | 60,4 | 58,8 | 48,6 | 30,2 | B |
| (17) | 9,6 | 56,8 | 64,2 | 52,4 | 46,8 | A |
| | 15,2 | 46,4 | 34,2 | 27,2 | 20,4 | B |
| (18) | 10,1 | 80,1 | 74,4 | 68,8 | 66,4 | A |
| | 14,2 | 67,8 | 46,2 | 44,2 | 34,6 | B |
| (19) | 11,6 | 74,2 | 64,4 | 58,9 | 50,1 | A |
| | 16,2 | 50,2 | 38,8 | 34,8 | 24,1 | B |
| (20) | 6,4 | 78,2 | 80,1 | 68,8 | 52,4 | A |
| | 12,1 | 60,4 | 52,2 | 36,4 | 28,2 | B |
| (21) | 10,1 | 92,1 | 78,8 | 68,4 | 58,9 | A |
| | 26,4 | 64,2 | 48,8 | 32,4 | 18,8 | B |
| (22) | 9,6 | 64,8 | 54,4 | 58,8 | 46,4 | A |
| | 8,8 | 60,0 | 38,8 | 28,2 | 12,6 | B |
| (23) | 18,2 | 81,6 | 78,8 | 68,6 | 54,2 | A |
| | 14,1 | 60,6 | 46,2 | 38,4 | 24,7 | B |

The above results show how DEAE-D exerts a strong inhibiting action on post-prandial hyperinsulinemia. This action occurs through the mobilization of the molecule at the duodenal-jejunum level of the lipid precursors.

The latter, which through the mediation of the gastroenterohormones induce insulin incretion, must be chelated to the intestinal lumen in great quantity; this necessitates the described dosage of 500 mg per 20 Kg body weight, and the administration schedule must take into account the contro-insular hormones. This mediation of the gastroenterohormones cited (CCK, secretion, GIP, etc.) is documented by the lack of response when fasting, that is, in the absence of stimulus by the lipid precursors.

I claim:

1. A method for decreasing hyperinsulinemia in humans comprising administering orally to a hyperinsulinemic subject an amount of diethylaminoethyldextran pharmaceutically effective to decrease the level of insulin in the blood.

2. The method of claim 1 wherein said effective amount is 500 mg per 20 Kg body weight.

3. The method of claim 1 for the treatment of endogenous and reactive hypoglycemia.

4. The method of claim 1 for the treatment of hyperinsulinemic and pre-clinical diabetes.

* * * * *